(12) United States Patent
Demmer et al.

(10) Patent No.: US 10,512,424 B2
(45) Date of Patent: Dec. 24, 2019

(54) METHOD AND APPARATUS FOR SELECTING ACTIVITY RESPONSE VECTOR

(71) Applicant: Medtronic, Inc., Minneapolis, MN (US)

(72) Inventors: Wade M Demmer, Coon Rapids, MN (US); Todd J Sheldon, North Oaks, MN (US)

(73) Assignee: Medtronic, Inc., Minneapolis, MN (US)

( * ) Notice: Subject to any disclaimer, the term of this patent is extended or adjusted under 35 U.S.C. 154(b) by 722 days.

(21) Appl. No.: 14/139,092

(22) Filed: Dec. 23, 2013

(65) Prior Publication Data

US 2015/0173655 A1 Jun. 25, 2015

(51) Int. Cl.
*A61B 5/11* (2006.01)
*A61B 5/00* (2006.01)
*A61N 1/365* (2006.01)

(52) U.S. Cl.
CPC ............ *A61B 5/1118* (2013.01); *A61B 5/686* (2013.01); *A61B 5/7221* (2013.01); *A61N 1/36542* (2013.01); *A61B 5/4836* (2013.01); *A61B 2562/0219* (2013.01); *A61N 1/36578* (2013.01)

(58) Field of Classification Search
CPC ..................................................... A61B 5/686
See application file for complete search history.

(56) References Cited

U.S. PATENT DOCUMENTS

| 761,162 A | 5/1904 | Gold |
|---|---|---|
| 4,374,382 A | 2/1983 | Markowitz |
| 4,476,868 A | 10/1984 | Thompson |
| 4,485,813 A | 12/1984 | Anderson |
| 5,052,388 A | 10/1991 | Sivula |
| 5,074,302 A | 12/1991 | Poore et al. |
| 5,117,824 A | 6/1992 | Keimel et al. |
| 5,154,170 A | 10/1992 | Bennett et al. |
| 5,165,404 A | 11/1992 | Andersson et al. |
| 5,165,405 A | 11/1992 | Eckwall |
| 5,172,690 A | 12/1992 | Nappholz et al. |

(Continued)

FOREIGN PATENT DOCUMENTS

| CN | 1838076 A | 9/2006 |
|---|---|---|
| EP | 1116495 A2 | 7/2001 |

(Continued)

OTHER PUBLICATIONS (PCT/US2015/062137) Invitation to Pay Additional fees and, where applicable, protest fee, mailed Mar. 1, 2016, 8 pages.

(Continued)

*Primary Examiner* — Daniel L Cerioni
*Assistant Examiner* — Yasmeen S Warsi

(57) ABSTRACT

A medical device and associated method evaluate vectors of a multi-dimensional accelerometer by receiving a signal from the accelerometer for each of the vectors and determining a metric from the signal for each of the vectors during a first sensing condition and during a second sensing condition. The difference between the metrics determined for the first sensing condition and the second sensing condition for each of the vectors is determined. One of the vectors is selected, based upon the determined differences, for monitoring the patient.

24 Claims, 11 Drawing Sheets

(56) References Cited

U.S. PATENT DOCUMENTS

| | | | |
|---|---|---|---|
| 5,190,034 A | 3/1993 | Sholder | |
| 5,222,493 A | 6/1993 | Sholder | |
| 5,226,413 A | 7/1993 | Bennett et al. | |
| 5,231,986 A | 8/1993 | Bennett | |
| 5,285,780 A | 2/1994 | Tsuji et al. | |
| 5,304,208 A | 4/1994 | Inguaggiato et al. | |
| 5,312,454 A | 5/1994 | Roline et al. | |
| 5,320,643 A | 6/1994 | Roline et al. | |
| 5,324,310 A | 6/1994 | Greeninger et al. | |
| 5,345,362 A | 9/1994 | Winkler | |
| 5,354,317 A | 10/1994 | Alt | |
| 5,423,867 A | 6/1995 | Poore et al. | |
| 5,447,525 A | 9/1995 | Powell et al. | |
| 5,496,351 A | 3/1996 | Plicchi et al. | |
| 5,507,782 A | 4/1996 | Kieval et al. | |
| 5,507,785 A | 4/1996 | Deno | |
| 5,562,711 A | 10/1996 | Yerich | |
| 5,593,431 A | 1/1997 | Sheldon | |
| 5,601,615 A | 2/1997 | Markowitz et al. | |
| 5,609,612 A | 3/1997 | Plicchi et al. | |
| 5,628,777 A | 5/1997 | Moberg et al. | |
| 5,683,432 A | 11/1997 | Goedeke et al. | |
| 5,693,075 A | 12/1997 | Plicchi et al. | |
| 5,720,769 A | 2/1998 | van Oort et al. | |
| 5,755,740 A | 5/1998 | Nappholz | |
| 5,766,230 A | 6/1998 | Routh et al. | |
| 5,782,889 A | 7/1998 | Hognelid et al. | |
| 5,944,745 A | 8/1999 | Rueter | |
| 5,954,755 A | 9/1999 | Casavant | |
| 6,044,297 A | 3/2000 | Sheldon | |
| 6,389,316 B1 | 5/2002 | Bornzin et al. | |
| 6,449,508 B1 | 9/2002 | Sheldon | |
| 6,553,259 B2 | 4/2003 | Mouchawar et al. | |
| 6,772,005 B2 | 8/2004 | Casavant et al. | |
| 6,819,955 B2 | 11/2004 | Levine | |
| 6,950,704 B1 | 9/2005 | Bradley | |
| 7,031,772 B2 | 4/2006 | Condie | |
| 7,076,283 B2 | 7/2006 | Cho et al. | |
| 7,130,690 B2 | 10/2006 | Rueter et al. | |
| 7,280,868 B2 | 10/2007 | Rueter et al. | |
| 7,400,924 B2 | 7/2008 | Rueter | |
| 7,457,666 B2 | 11/2008 | Bohn et al. | |
| 7,532,930 B2 | 5/2009 | Schermeier et al. | |
| 7,761,162 B2 | 7/2010 | Dong et al. | |
| 7,778,696 B2 | 8/2010 | Sathaye | |
| 7,783,355 B2 | 8/2010 | Rueter | |
| 7,818,059 B2 | 10/2010 | Rueter et al. | |
| 7,831,303 B2 | 11/2010 | Rueter et al. | |
| 8,280,509 B2 | 10/2012 | Sathaye | |
| 8,401,666 B2 * | 3/2013 | Skelton | A61B 5/1116 607/17 |
| 8,433,409 B2 | 4/2013 | Johnson | |
| 8,532,785 B1 | 9/2013 | Crutchfield et al. | |
| 8,541,131 B2 | 9/2013 | Lund et al. | |
| 8,956,295 B2 | 2/2015 | Ni et al. | |
| 9,452,292 B2 | 9/2016 | Demmer et al. | |
| 2002/0183798 A1 | 12/2002 | Vonk | |
| 2003/0069611 A1 | 4/2003 | Levine | |
| 2003/0078624 A1 | 4/2003 | Carlson | |
| 2003/0078627 A1 | 4/2003 | Casavant et al. | |
| 2003/0083700 A1 | 5/2003 | Hill | |
| 2003/0083712 A1 | 5/2003 | Rueter et al. | |
| 2003/0195579 A1 | 10/2003 | Bradley et al. | |
| 2003/0204214 A1 | 10/2003 | Ferek-Patric | |
| 2004/0030358 A1 | 2/2004 | Rueter et al. | |
| 2004/0088019 A1 | 5/2004 | Rueter et al. | |
| 2004/0260352 A1 | 12/2004 | Rueter et al. | |
| 2005/0015985 A1 | 1/2005 | Dvoskin | |
| 2005/0021095 A1 | 1/2005 | Rueter et al. | |
| 2005/0159785 A1 | 7/2005 | Rueter | |
| 2005/0222630 A1 | 10/2005 | Schermeier et al. | |
| 2006/0155338 A1 | 7/2006 | Mongeon et al. | |
| 2006/0241710 A1 | 10/2006 | Rueter | |
| 2006/0247705 A1 | 11/2006 | Rueter et al. | |
| 2006/0253156 A1 | 11/2006 | Pastore et al. | |
| 2007/0115277 A1 | 5/2007 | Wang et al. | |
| 2008/0195165 A1 | 8/2008 | Stahmann et al. | |
| 2010/0010380 A1 | 1/2010 | Panken et al. | |
| 2010/0010583 A1 | 1/2010 | Panken et al. | |
| 2011/0012759 A1 | 1/2011 | Yin | |
| 2011/0029034 A1 | 2/2011 | Fischer | |
| 2011/0152963 A1 | 6/2011 | Stahmann et al. | |
| 2012/0065524 A1 | 3/2012 | Morren et al. | |
| 2012/0109259 A1 | 5/2012 | Bond et al. | |
| 2012/0172892 A1 | 7/2012 | Grubac | |
| 2012/0245476 A1 | 9/2012 | Skerl et al. | |
| 2013/0035748 A1 | 2/2013 | Bonner et al. | |
| 2013/0079861 A1 | 3/2013 | Reinert et al. | |
| 2013/0090702 A1 | 4/2013 | Mongeon et al. | |
| 2013/0116602 A1 | 5/2013 | Van Den Heuvel et al. | |
| 2013/0150911 A1 | 6/2013 | Perschbacher et al. | |
| 2013/0211205 A1 * | 8/2013 | Havel | A61B 5/721 600/301 |
| 2013/0289652 A1 | 10/2013 | Skelton et al. | |
| 2015/0173655 A1 | 6/2015 | Demmer et al. | |
| 2015/0217119 A1 | 8/2015 | Nikolski et al. | |
| 2015/0238769 A1 | 8/2015 | Demmer et al. | |
| 2016/0144191 A1 | 5/2016 | Sheldon et al. | |

FOREIGN PATENT DOCUMENTS

| | | |
|---|---|---|
| EP | 2239007 A1 | 10/2010 |
| NO | 2004/041086 A1 | 5/2004 |

OTHER PUBLICATIONS (PCT/US2015/062137) Invitation to Pay Additional Fees and, where applicable, protest fee.
U.S. Appl. No. 14/174,514, filed Feb. 6, 2014.
(PCT/US2015/013729) PCT Notification of Transmittal of the International Search Report and the Written Opinion of the International Searching Authority.
(PCT/US2014/070598) PCT Notification of Transmittal of the International Search Report and the Written Opinion of the International Searching Authority.
Demmer, et al., "Method and Apparatus for Detecting Loss of Capture", U.S. Appl. No. 14/261,776, filed Apr. 25, 2014, 44 pages.
(PCT/US2014/067337) PCT Notification of Transmittal of the International Search Report and the Written Opinion of the International Searching Authority.
U.S. Appl. No. 14/552,758, filed Nov. 25, 2014.
(PCT/US2015/027055) PCT Notification of Transmittal of the International Search Report and the Written Opinion of the International Searching Authority, dated Sep. 30, 2015, 9 pages.
Telectronics Meta 1254 DDDr Physician Manual, Chapter 8 (46 pages).
Telectronics Meta 1254 DDDr Physician Manual (55 pages).
Sheldon et al, "Rate Responsive Cardiac Pacing Control Using Posture", U.S. Appl. No. 14/920,228, filed Oct. 22, 2015, 54 pages.
(PCT/US2016/049573) PCT Notification of Transmittal of the International Search Report and the Written Opinion of the International Searching Authority, dated Nov. 28, 2016, 10 pages.

* cited by examiner

METHOD AND APPARATUS FOR SELECTING ACTIVITY RESPONSE VECTOR

TECHNICAL FIELD

The disclosure relates to implantable medical devices having multi-dimensional sensors and an associated method for determining an optimal signal vector of the multi-dimensional sensor.

BACKGROUND

Numerous implantable medical devices (IMDs) are available for acute or chronic implantation within patients. Some implantable medical devices may be used to monitor physiological signals of the patient, such as cardiac pacemakers, implantable hemodynamic monitors, implantable cardiac monitors (sometimes referred to as implantable loop recorders or ECG monitors), implantable blood chemistry monitors, implantable pressure monitors, etc. Among the various types of physiological sensors utilized by medical devices for monitoring patients are electrodes for measuring electrical signals and/or impedances, piezoelectric crystals, accelerometers, pressure sensors, pH sensors, acoustical sensors, temperature sensors, and oxygen sensors.

The physiological signals may be stored, processed and analyzed by the medical device to generate physiological data about a patient useful to a clinician in diagnosing a condition or planning medical treatment. Some implantable devices may be configured to deliver a therapy in conjunction with monitoring of physiological signals. Physiological signals may be processed and analyzed to determine when a therapy is needed or how a therapy needs to be adjusted to benefit the patient. Therapies delivered by an implantable medical device can include electrical stimulation therapies, e.g., cardiac pacing, cardioversion/defibrillation shock pulses, or neurostimulation, and pharmacological or biological fluid delivery therapies.

In order to provide reliable physiological data needed for determining a medical risk, detecting pathological conditions, controlling automatic therapy delivery or generally producing data in a form useful to a clinician for diagnosis and prognosis, reliable sensor signals are required. For example, patient activity level may be determined from an accelerometer in order provide rate responsive pacing at a heart rate that meets the metabolic demand of the patient. An accelerometer signal may be subject to noise or motion not directly associated with the motion of the patient activity or exercise, such as cardiac motion or respiratory motion. Methods are needed for identifying a sensor signal that provides acceptable signal to noise ratio for reliable signal processing.

DETAILED DESCRIPTION

Figure 1:
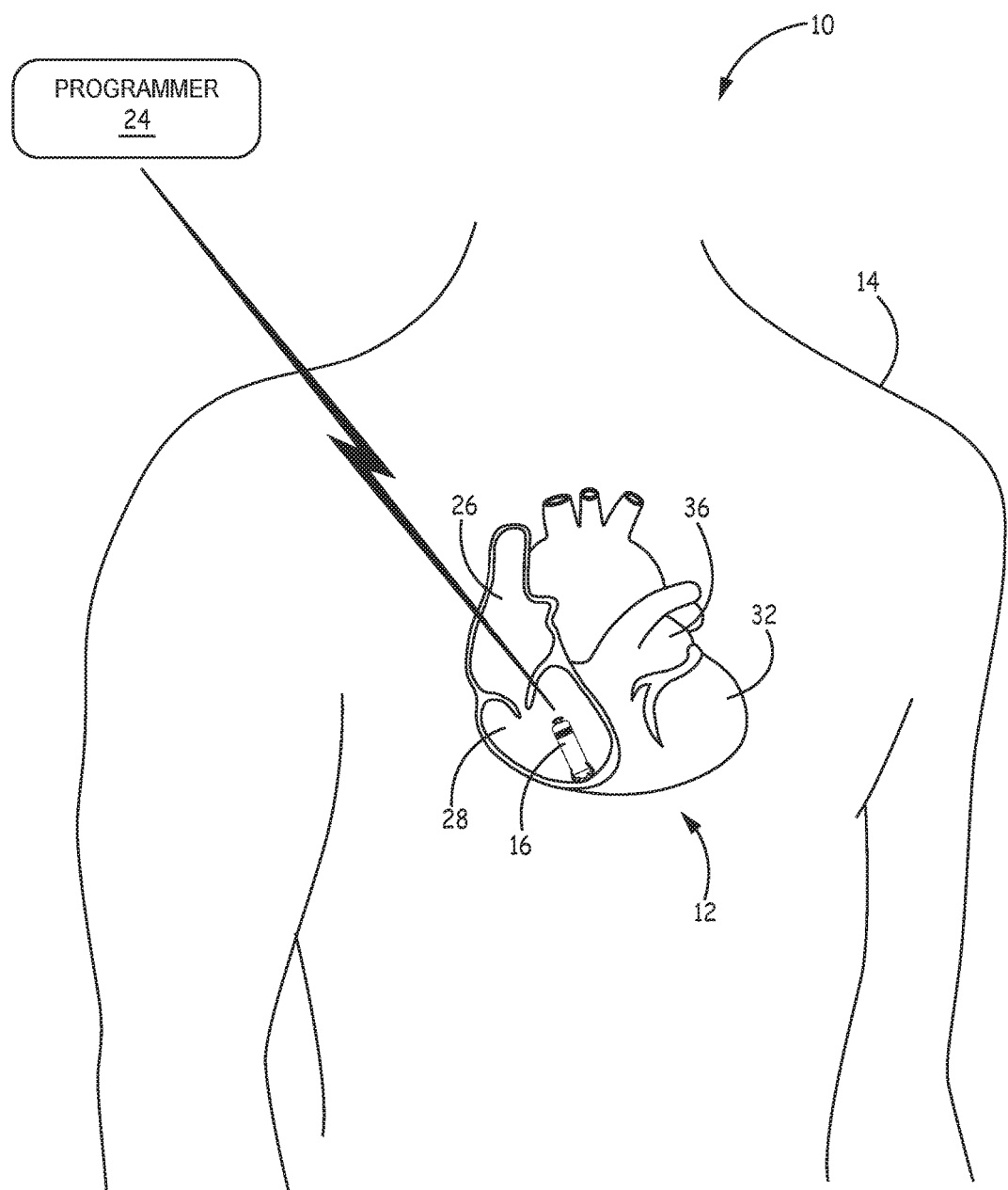
FIG. 1 is a conceptual diagram illustrating one therapy system that may be used to monitor one or more physiological parameters of a patient and provide therapy.

FIG. 1 is a conceptual diagram illustrating one therapy system 10 that may be used to monitor one or more physiological parameters of patient 14 and/or to provide therapy to heart 12 of patient 14. Therapy system 10 includes IMD 16, configured to communicate wirelessly with programmer 24. IMD 16 is an implantable leadless pacemaker that is capable of providing electrical signals to heart 12 via one or more electrodes (not shown in FIG. 1) on its outer housing. Additionally, IMD 16 may sense electrical signals attendant to the depolarization and repolarization of heart 12 via electrodes on its outer housing. In some examples, IMD 16 provides pacing pulses to heart 12 based on the electrical signals sensed within heart 12.

IMD 16 includes a set of active fixation tines to secure IMD 16 to a patient tissue. IMD 16 may include a set of active fixation tines as disclosed in commonly-assigned, pre-grant publication U.S. 2012/0172892 (Grubac, et al.), hereby incorporated herein by reference in its entirety. In the example of FIG. 1, IMD 16 is positioned wholly within heart 12 proximate to an inner wall of right ventricle 28 to provide right ventricular (RV) pacing. Although IMD 16 is shown within heart 12 and proximate to an inner wall of right ventricle 28 in the example of FIG. 1, IMD 16 may be positioned at any other location outside or within heart 12. For example, IMD 16 may be positioned outside or within right atrium 26, left atrium 36, and/or left ventricle 32, e.g., to provide right atrial, left atrial, and left ventricular pacing, respectively.

Depending on the location of implant, IMD 16 may include other stimulation functionalities. For example, IMD 16 may provide atrioventricular nodal stimulation, fat pad stimulation, vagal stimulation, or other types of neurostimulation. In other examples, IMD 16 may be a monitor that senses one or more parameters of heart 12 and may not provide any stimulation functionality. In some examples, system 10 may include a plurality of leadless IMDs 16, e.g., to provide stimulation and/or sensing at a variety of locations.

FIG. 1 further depicts programmer 24 in wireless communication with IMD 16. In some examples, programmer 24 comprises a handheld computing device, computer workstation, or networked computing device. Programmer 24 includes a user interface that presents information to and receives input from a user. It should be noted that the user may also interact with programmer 24 remotely via a networked computing device.

A user, such as a physician, technician, surgeon, electrophysiologist, other clinician, or patient, interacts with programmer 24 to communicate with IMD 16. For example, the user may interact with programmer 24 to retrieve physiological or diagnostic information from IMD 16. A user may also interact with programmer 24 to program IMD 16, e.g., select values for operational parameters of the IMD 16. The user may use programmer 24 to retrieve information from IMD 16 regarding the rhythm of heart 12, trends therein over time, arrhythmic episodes, patient activity and trends in patient activity.

As an example, the user may use programmer 24 to retrieve information from IMD 16 regarding other sensed physiological parameters of patient 14 or information derived from sensed physiological parameters, such as intracardiac or intravascular pressure, activity, posture, tissue oxygen levels, blood oxygen levels, respiration, tissue perfusion, heart sounds, cardiac electrogram (EGM), intracardiac impedance, or thoracic impedance. In some examples, the user may use programmer 24 to retrieve information from IMD 16 regarding the performance or integrity of IMD 16 or other components of system 10, or a power source of IMD 16. As another example, the user may interact with programmer 24 to program, e.g., select parameters for, therapies provided by IMD 16, such as pacing and, optionally, neurostimulation.

IMD 16 and programmer 24 may communicate via wireless communication. Examples of communication techniques may include, for example, low frequency or radiofrequency (RF) telemetry, but other techniques are also contemplated. In some examples, programmer 24 may include a programming head that may be placed proximate to the patient's body near the IMD 16 implant site in order to improve the quality or security of communication between IMD 16 and programmer 24.

IMD 16 further includes a three-dimensional accelerometer (not shown in FIG. 1) capable of producing motion signals in three different dimensions. For example, the accelerometer may produce signals corresponding to motion in three orthogonal vectors, x, y and z. Upon implantation of IMD 16, the orientation of the three orthogonal vectors relative to the patient's anatomy will be uncertain since rotation of the IMD 16 can occur during an implant procedure. Furthermore, the IMD 16 orientation relative to the patient's anatomy may change over time as the IMD 16 is subjected to cardiac motion and postural changes for example. As such, an accelerometer vector providing the optimal signal-to-noise ratio may be unknown, will vary between patients and may vary within a given patient over time due to changes in position of IMD 16 and/or changes in patient posture or other factors.

While a single-chamber leadless device is shown in FIG. 1, it is recognized that techniques disclosed herein may be implemented in numerous types of implantable medical devices or combinations of implantable medical devices configured for monitoring a patient and/or delivering a therapy. Techniques disclosed herein may be applied to any medical sensor or combination of sensors having multiple vectors or axes for sensing a signal used to monitor a patient. Such sensors may be included in cardiac monitors, hemodynamic monitors, pacemakers, implantable cardioverter defibrillators, neurostimulators, drug delivery pumps, or other medical devices that are implantable or worn by a patient. The disclosed techniques are particularly useful in selecting an axis or vector of a multi-axis motion sensor.

Figure 2:
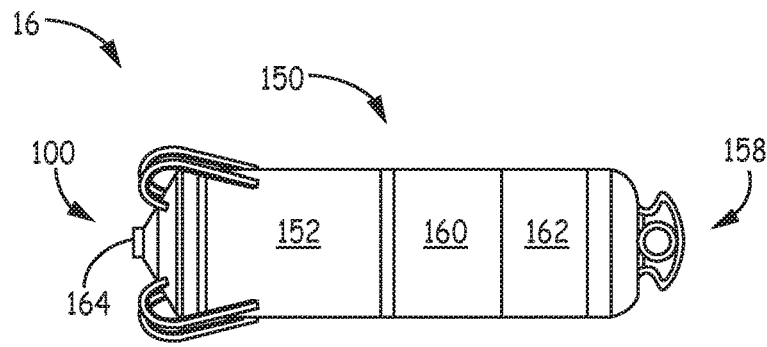
FIG. 2 is one example of an IMD in which techniques disclosed herein may be implemented.

FIG. 2 is a conceptual drawing of leadless IMD 16 including tine fixation and electrode subassembly 100, electronic subassembly 150 and delivery tool interface 158. Delivery tool interface 158 is located at the proximal end of electronic subassembly 150. Delivery tool interface 158 is configured to connect to a delivery device, such as a catheter, used to position IMD 16 during an implantation procedure, for example within a heart chamber.

Electronic subassembly 150 includes control electronics 152, which controls the sensing and/or therapy functions of IMD 16, and battery 160, which powers control electronics 152. Battery 160 may include features of the batteries disclosed in commonly-assigned U.S. Pat. No. 8,433,409 (Johnson, et al.), the entire contents of which are incorporated by reference herein. As one example, control electronics 152 includes sensing circuitry, a stimulation generator and a telemetry module. Control electronics 152 includes a three-dimensional accelerometer in one embodiment for monitoring patient activity for use in controlling rate-responsive pacing in patient 14.

Tine fixation subassembly 100 is configured to anchor leadless IMD 16 to a patient tissue, such as a wall of heart 12, to position electrode 164 in operative proximity to a targeted tissue for sensing electrical signals and/or delivering electrical stimulation pulses. When IMD 16 is advanced transvenously into the right ventricle, as shown in FIG. 1 for example, the orientation of IMD 16 may vary and the final orientation of an accelerometer included in control electronics 152 relative to the patient's anatomy may be unknown and may fluctuate with body movement and cardiac movement as described above. When the accelerometer is being used to monitor patient body motion to detect changes in activity as an indication of changes in metabolic demand, significant artifact will be present in the accelerometer signal due to cardiac motion. The techniques disclosed herein may be used to select an accelerometer vector for monitoring patient body motion that has an acceptable signal to noise ratio for distinguishing between different levels of patient activity in the presence of cardiac or other motion artifact that may confound the motion signal of interest.

The housings of control electronics 152 and battery 160 are formed from a biocompatible material, such as a stainless steel or titanium alloy. In some examples, the housings of control electronics 152 and battery 160 may include an insulating coating. Examples of insulating coatings include parylene, urethane, PEEK, or polyimide among others. Electronic subassembly 150 further includes electrode 162, which may include a low polarizing coating, such as titanium nitride, iridium oxide, ruthenium oxide among others. The entirety of the housings of control electronics 152 and battery 160 are electrically connected to one another, but only electrode 162 and electrode 164 are uninsulated. Electrodes 162 and 164 form an anode and cathode pair, respectively for bipolar cardiac sensing and pacing. In other examples, the entirety of the housing of battery 160 or the entirety of the housing of electronic subassembly 150 may function as an electrode instead of providing a localized electrode such as electrode 162. Alternatively, electrode 162 may be electrically isolated from the other portions of the housings of control electronics 152 and battery 160.

Figure 3:
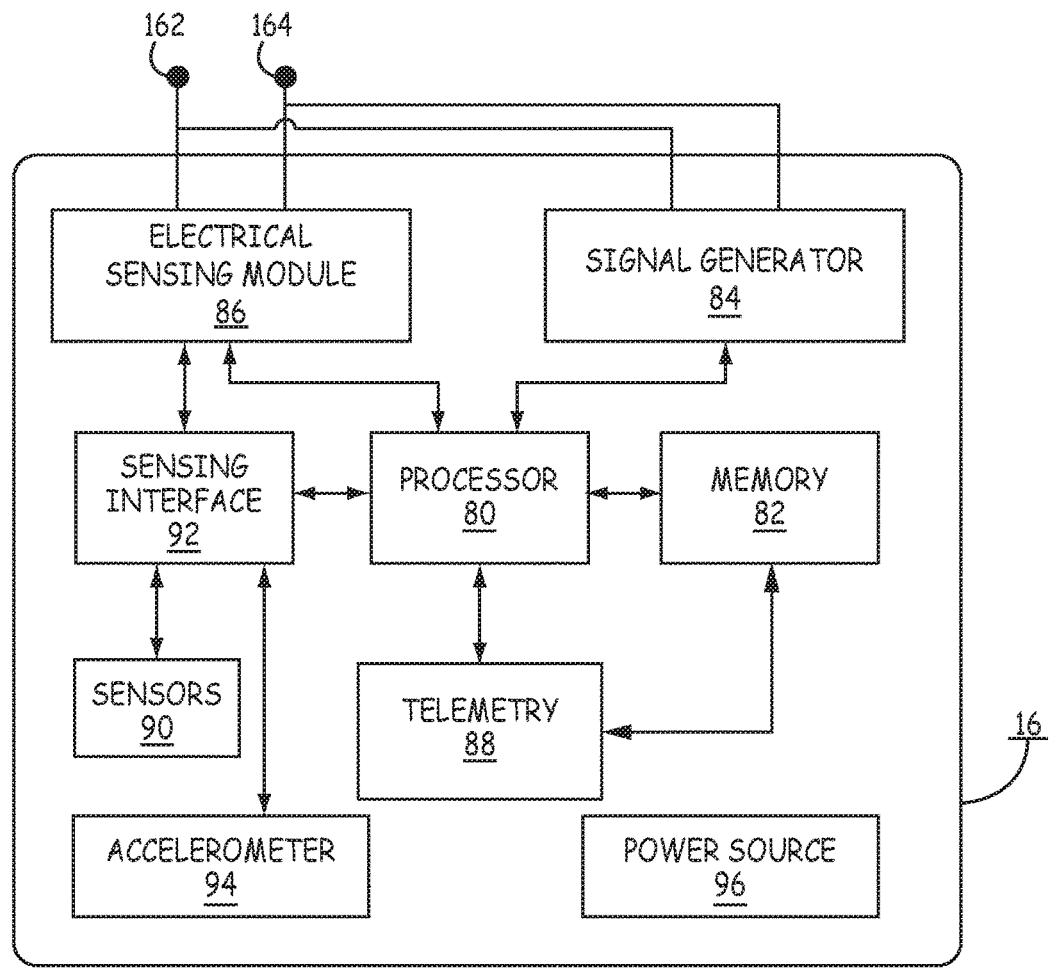
FIG. 3 is a functional block diagram of an example configuration of the IMD of FIG. 2.

FIG. 3 is a functional block diagram of an example configuration of IMD 16. IMD 16 includes a processor and control module 80, also referred to herein as "processor" 80, memory 82, signal generator 84, electrical sensing module 86, and telemetry module 88. IMD 16 additionally includes a multi-dimensional accelerometer 94 for detecting patient body motion for monitoring patient activity. In various examples, accelerometer 94 may be implemented as a DC or AC accelerometer, a piezoelectric, piezoresistive or capacitive sensor or a micro electro-mechanical systems (MEMS) device.

Accelerometer 94 may be bonded to an inner surface of the control electronics enclosure or incorporated on an internal substrate. A pacemaker arrangement including a piezoelectric accelerometer for detecting patient motion is disclosed, for example, in U.S. Pat. No. 4,485,813 (Anderson, et al.) and U.S. Pat. No. 5,052,388 (Sivula, et al.), both of which patents are hereby incorporated by reference herein in their entirety. Examples of three-dimensional accelerometers used for sensing patient activity and/or posture are generally described in U.S. Pat. No. 5,593,431 (Sheldon), and U.S. Pat. No. 6,044,297 (Sheldon), both of which are hereby incorporated herein by reference in their entirety. The techniques disclosed herein can be implemented in conjunction with a variety of three-dimensional accelerometers. Generally, three one-dimensional accelerometers are arranged to respond to acceleration in three different vectors, typically but not necessarily orthogonal vectors, in three dimensional space.

An accelerometer signal used for monitoring patient activity may be analyzed for providing sensor-indicated pacing rate for controlling rate responsive cardiac pacing according to patient metabolic demand. Control of rate responsive pacing using an activity sensor is generally disclosed in commonly-assigned U.S. Pat. No. 7,031,772 (Condie, et al.), hereby incorporated herein by reference in its entirety. An accelerometer signal may additionally or alternatively be used for monitoring patient activity for other patient monitoring, therapy control or diagnostic purposes. Accelerometer 94 may additionally be used to determine patient posture, cardiac motion, respiratory motion or other physiological movement.

IMD 16 optionally includes other physiological sensors 90, which may include pressure sensors, pH sensors, temperature sensors, acoustical sensors, flow sensors, oxygen sensors, or any other sensor used for producing a signal responsive to a time-varying physiological condition. Accelerometer 94 and sensors 90 are shown schematically within IMD 16, however it is recognized that accelerometer 94 and sensors 90 may alternatively be carried by a lead extending from IMD 16 or mounted along the exterior of the IMD electronic subassembly 152.

Modules 80, 84, 86, 88, 92, memory 82, sensors 90, and accelerometer 94 shown in FIG. 3 may include any discrete and/or integrated electronic circuit components that implement analog and/or digital circuits capable of producing the functions attributed to IMD 16 herein. For example, sensing module 86, sensing interface 92, and processor and control module 80 may include analog circuits, e.g., amplification circuits, filtering circuits, and/or other analog circuitry for receiving and processing signals from electrodes 162 and 164, sensors 90 and accelerometer 94. Sensing module 86, sensing interface 92 and processing and control module 80 may also include digital circuits, e.g., combinational or sequential logic circuits, memory devices, A/D converters, etc. for processing received signals.

The functions attributed to IMD 16 herein may be embodied as one or more processors, hardware, firmware, software, or any combination thereof. Processor and control module 80 may include any one or more of a microprocessor, a controller, a digital signal processor (DSP), an application specific integrated circuit (ASIC), a field-programmable gate array (FPGA), or equivalent discrete or integrated logic circuitry. In some examples, processor 80 may include multiple components, such as any combination of one or more microprocessors, one or more controllers, one or more DSPs, one or more ASICs, or one or more FPGAs, as well as other discrete or integrated logic circuitry. Depiction of different features as discrete modules or components is intended to highlight different functional aspects and does not necessarily imply that such modules must be realized by separate hardware or software components. Rather, functionality associated with one or more modules may be performed by separate hardware or software components, or integrated within common or separate hardware or software components. For example, sensing interface 92 for receiving and converting analog electrical signals received from other IMD modules or sensors may be implemented in hardware and software included in processor 80 and memory 82.

Sensing interface 92 is configured to receive one or more analog signals from electrical sensing module 86, sensors 90, and/or accelerometer 94. Sensing interface 92 includes an A/D converter for converting analog signals to digital signals. Processor 80 receives the converted digital signals and may analyze the digital signals for detecting a patient condition, controlling a therapy delivered by signal generator 84, and/or storing patient data in memory 82 for later transmission to programmer 24 via telemetry module 88.

A power source 96 provides power to each of the other modules and components of IMD 16 as required. Processor 80 may execute power control operations to control when various components or modules are powered to perform various IMD functions. Power source 96 may include one or more energy storage devices, such as one or more rechargeable or non-rechargeable batteries. Processor 80 may also be configured to perform diagnostic testing of IMD 16, which may include monitoring the remaining charge of power source 96 and providing a replacement or recharge indicator, for example. The connections between power source 96 and processor 80 and other IMD modules and components are not shown for the sake of clarity.

Memory 82 may include computer-readable instructions that, when executed by processor 80, cause IMD 16 and processor 80 to perform various functions attributed throughout this disclosure to IMD 16, processor 80, and sensing interface 92. The computer-readable instructions may be encoded within memory 82. Memory 82 may include any non-transitory, computer-readable storage media including any volatile, non-volatile, magnetic, optical, or electrical media, such as a random access memory (RAM), read-only memory (ROM), non-volatile RAM (NVRAM), electrically-erasable programmable ROM (EEPROM), flash memory, or other digital media with the sole exception being a transitory propagating signal.

Electrical sensing module 86 monitors cardiac electrical signals for sensing cardiac electrical events, e.g. P-waves and R-waves, from the electrodes in order to monitor electrical activity of heart 112. Sense signal are used by processor 80 to determine a need for therapy delivery. Processor and control module 80 includes a therapy control module that controls signal generator 84 to deliver electrical stimulation therapy, e.g., cardiac pacing, to heart 12 according to a selected one or more therapy programs, which may be stored in memory 82. Signal generator 84 is electrically coupled to electrodes 162 and 164, to deliver electrical stimulation therapy to heart 12. Signal generator 84 delivers cardiac pacing pulses according to therapy control parameters and responsive to signals sensed by electrical sensing module 86, sensors 90, and accelerometer 94. Memory 82 stores intervals, counters, or other data used by processor 80 to control the delivery of pacing pulses by signal generator 84. In one example, IMD 16 is a rate responsive pacemaker that utilizes a patient activity metric derived by processor 80 from a signal received from accelerometer 94 for controlling a rate of pacing therapy delivery by signal generator 84.

As described below, processor 80 may automatically adjust a therapy delivery rate and automatically adjust rate control parameters based on patient activity monitoring performed using a selected accelerometer vector signal. The processor 80 is configured to evaluate the available accelerometer vector signals and select a vector for monitoring patient activity. A patient activity metric is determined from the selected accelerometer vector signal at predetermined intervals of time. The therapy control module included in processor 80 adjusts a therapy control parameter in response to the metric.

In one embodiment, processor 80 generates a historical profile of the activity metric and automatically adjusts a control parameter used to set a target rate of therapy delivery in response to the historical profile. For example a historical level of the activity metric determined for non-strenuous activities of daily living may be used to set a target pacing rate for activities of daily living. The processor compares the automatically adjusted target rate to an expected trend. For example, the processor may determine if the target rate has been sequentially reduced or increased n successive times or become within a minimum range of a lower pacing rate or an upper pacing rate. Such trends in the target rate are not expected under optimal pacing conditions. If the target rate adjustments fail to meet expected trend criteria, the processor triggers an evaluation of the accelerometer vector signals to determine if a more optimal vector signal is available than the currently selected vector signal.

Figure 4:
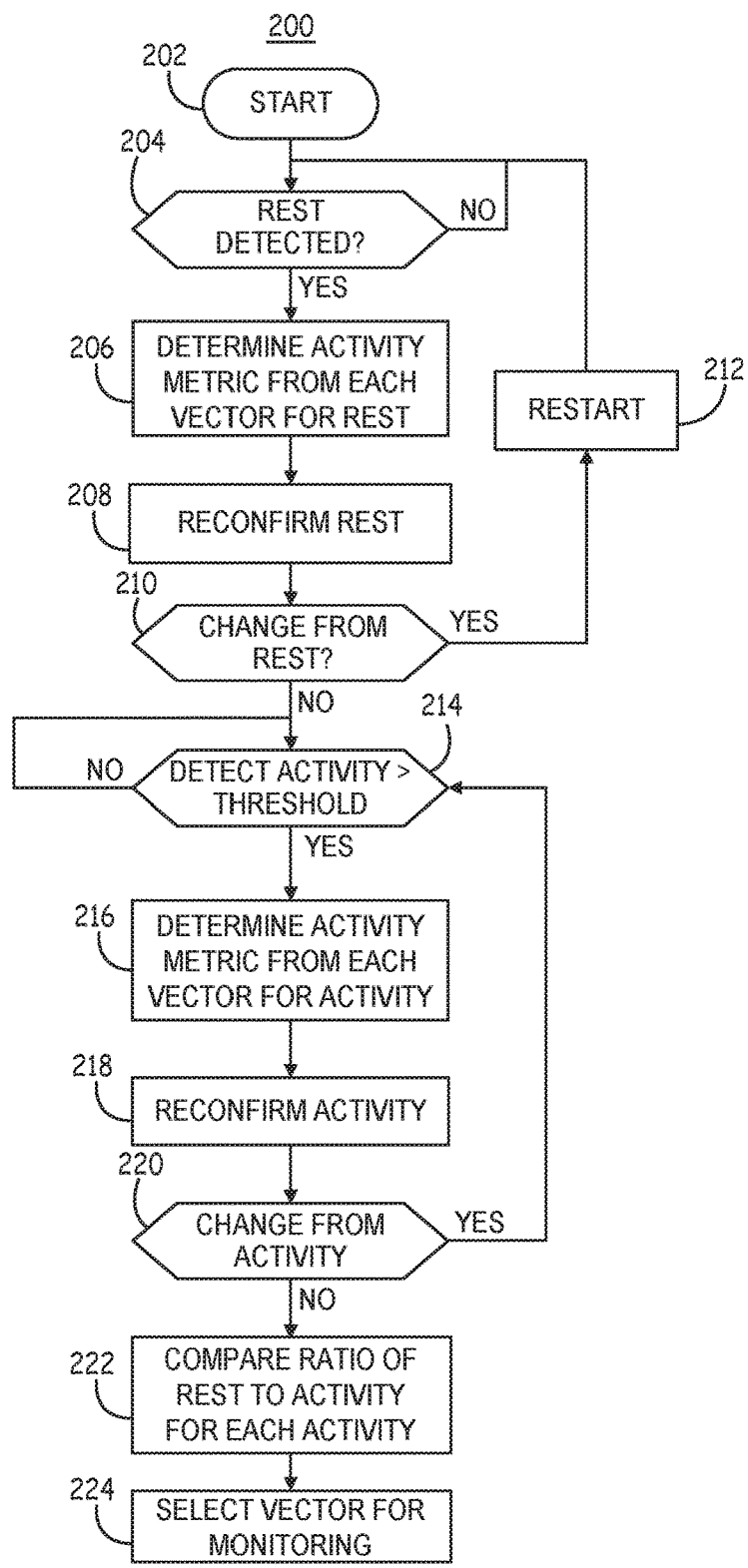
FIG. 4 is a flow chart of a method for selecting a sensor vector according to one embodiment.

FIG. 4 is a flow chart 200 of a method for selecting an accelerometer signal vector according to one embodiment. The process is started at block 202, which may be manually initiated by a user, performed on a periodic scheduled basis, or in response to a trigger. Various triggers for starting a vector evaluation process will be described in greater detail below.

The method described in conjunction with flow chart 200 and other flow charts presented herein relates primarily to a three-dimensional accelerometer used for monitoring patient activity. The three dimensions may be orthogonal vectors corresponding to an x-axis, y-axis and a z-axis of the accelerometer where the orientation of these axes are unknown relative to a patient's anatomy. The three vectors are not limited to being orthogonal vectors, however. In various examples, a multi-dimensional accelerometer may be configured to sense motion along two or more orthogonal or non-orthogonal vectors. While the illustrative examples presented herein relate to a three-dimensional accelerometer used for monitoring patient activity, it is contemplated that the techniques disclosed herein may be implemented in conjunction with multi-dimensional accelerometers used for monitoring other motion signals or with other types of multi-vector sensors used for monitoring a patient.

At block 204, the IMD processor determines if the patient is in a resting state. This determination may be made based on user input, time of day, or other physiological signals such as heart rate, respiration rate and/or posture. In one example a resting state, also referred to herein as a "resting condition," is determined from an accelerometer vector signal. Whichever accelerometer vector is presently selected for monitoring patient activity, a nominal vector, or a combination of the available vector signals may be used to detect rest.

Various activity metrics may be derived from the accelerometer signal that are correlated to patient activity. In the illustrative embodiments described herein, the activity metric derived from the accelerometer signal is obtained by integrating the absolute value of a selected accelerometer vector signal over a predetermined time duration (such as 2 seconds). This metric is referred to herein as an "activity count" and is a representation of the amount of activity detected during the predetermined time interval. The 2-second (or other time interval) counts can be used directly to indicate patient activity in some embodiments or combined in further calculations to obtain other activity metrics. For example, the 2-second interval counts may be averaged or summed over multiple intervals to determine a patient activity level at a particular monitoring interval or for establishing an activity profile over a period of time.

One example of obtaining an activity count is disclosed in commonly-assigned U.S. Pat. No. 6,449,508 (Sheldon, et al.), incorporated herein by reference in its entirety. In another example, an activity count for use in rate responsive pacing is generally disclosed in U.S. Pat. No. 5,562,711 (Yerich, et al.), hereby incorporated herein by reference in its entirety. Briefly, an activity count is determined as a count of the number of times the accelerometer signal peak is greater than a predetermined threshold during a predetermined time interval. Other methods for using an accelerometer for monitoring patient activity for controlling pacing rate are generally disclosed in pre-grant U.S. Publication No. 20030078624 (Carlson, et al.).

Once a resting contion of the patient is detected, a metric used to represent patient activity is derived from the accelerometer signal for each of the available accelerometer vectors at block 206. This may be done for all three vectors of the three-dimensional accelerometer simultaneously if the IMD is configured to sense and process all three vector signals simultaneously. In other embodiments, the IMD may be configured to sense and process only one vector signal at a time. In either case, after determining an activity metric for all three vectors, the resting condition may be reconfirmed at block 208 to ensure that the patient's activity level did not change, as determined at block 210, during the acquisition of the activity metrics for each vector during a resting condition. The IMD processor may determine the activity metric from the same vector(s) used to detect rest at block 204 to verify the activity metric has not changed from a resting level. If it has changed, the results obtained so far may be discarded and the process may restart at block 212 by returning to block 204 to await detection of a resting condition again.

If resting metrics are successfully determined for each vector during a detected and verified resting condition, the process advances to block 214 to wait for the patient's activity to change from the resting level to a non-resting or active level. A predetermined activity threshold may be defined which must be met in order to begin acquiring activity metrics for each vector at block 216. All three vectors may be processed simultaneously to derive an activity metric for all three vectors during the non-resting condition. The processor may reconfirm that the patient activity level at block 218 to validate the data acquisition for a confirmed period of non-resting patient activity. If the patient activity level detected at block 214, which was required to start activity data acquisition at block 216, is still present after deriving the activity metrics for all vectors, as determined at block 220, the activity metrics are deemed valid. If the patient activity level is not the same, e.g., has fallen below the threshold or changed by more than some percentage from the level detected at block 214, the activity metrics may be deemed invalid, and the process is repeated until valid data is obtained.

Once a resting metric and a non-resting metric are obtained for each vector, a ratio or difference between the resting metric and the non-resting metric are determined for each vector at block 222. The vector having the greatest difference between rest and activity is selected for monitoring patient activity at block 224. The vector having the greatest difference is expected to have the greatest signal-to-noise ratio and enable changes in activity to be reliably detected for use in controlling rate responsive pacing, for example. Patient body motion indicative of activity is discernable from cardiac motion on a single vector that has the greatest difference between a metric obtained at rest and one obtained during activity. In other examples, other criteria may be applied to the resting and non-resting activity metrics under evaluation for selecting an acceptable vector for patient monitoring. Other criteria may include comparisons between vectors and/or comparisons to other sensor signals.

Figure 5A:
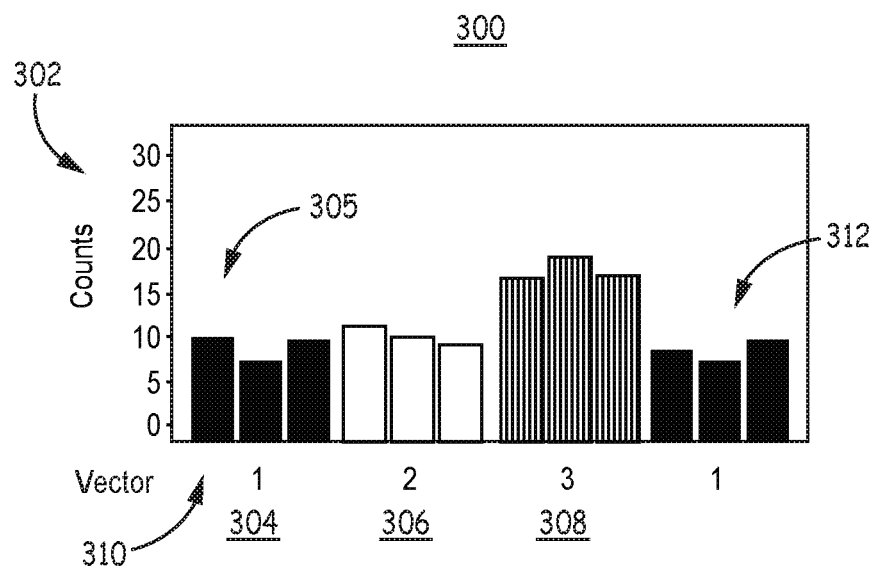
FIGS. 5A and 5B are example bar graphs illustrating activity metrics determined as activity counts for three different accelerometer vectors.

FIG. 5A is an example bar graph 300 illustrating activity metrics determined as counts shown along the Y-axis 302 for three different accelerometer vectors 304, 306 and 308 shown along the X-axis 310. Vector 1 304 is used for initial rest detection and activity counts are determined for Vector 1 over three different time intervals (represented by the three bars) during patient rest. Similarly, the activity metric is determined for three time intervals for Vectors 2 (306) and 3 (308). The time intervals for determining activity metrics for a given vector may be consecutive as the vectors are selected one at a time. Alternatively, time intervals for determining activity metrics for a given vector may be non-consecutive. For example, activity counts may be determined over 2 second intervals for each vector sequentially and that process is repeated 3 times to obtain three metrics for each vector.

In this example, Vector 1 (304) is used for initially detecting a resting condition for enabling resting data acquisition. After obtaining activity metrics, in this example activity counts, for the desired number of time intervals for each vector, the resting condition is reconfirmed by determining the activity metric for Vector 1 again at 312. If the average activity counts for Vector 1 determined at 312 have changed significantly since initially detecting rest at 305, e.g. by more than a predetermined percentage such as 10%, the activity metrics determined for rest may be discarded and the process may be restarted as described above. In particular, if the average activity metric has increased indicating the patient is no longer in a resting state, data acquisition for the resting condition may need to be repeated in order to obtain reliable resting condition activity metrics for each vector.

Figure 5B:
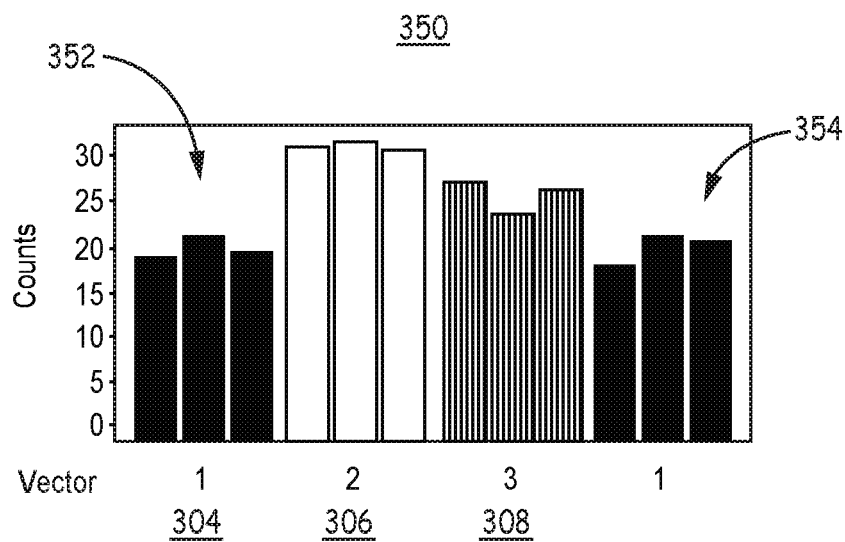

FIG. 5B is an example bar graph 350 depicting activity metrics determined for each vector 304, 306 and 308 during activity. Vector 1 304 is used to detect activity above a threshold level at 352 to initiate data acquisition during non-resting activity. As described above, activity counts may be determined for each vector during consecutive or non-consecutive time intervals for each of the three vectors. After obtaining activity counts for each vector for the desired number of time intervals, the activity level based on Vector 1 (304) is reconfirmed at 354 to verify that the patient activity has stayed within a predetermined range of the initial activity level detected at 352. After obtaining activity metrics for all vectors during both rest and non-resting conditions, an average ratio or difference between the resting activity metric and the non-resting activity metric is determined for each vector. The vector having the greatest difference between rest and activity is selected for monitoring patient activity. In this example, Vector 2 has an activity-to-rest ratio of roughly 3:1 which leads to selection of Vector 2 for patient monitoring over Vectors 1 and 3, which each have a ratio of roughly 2:1.

Figure 6:
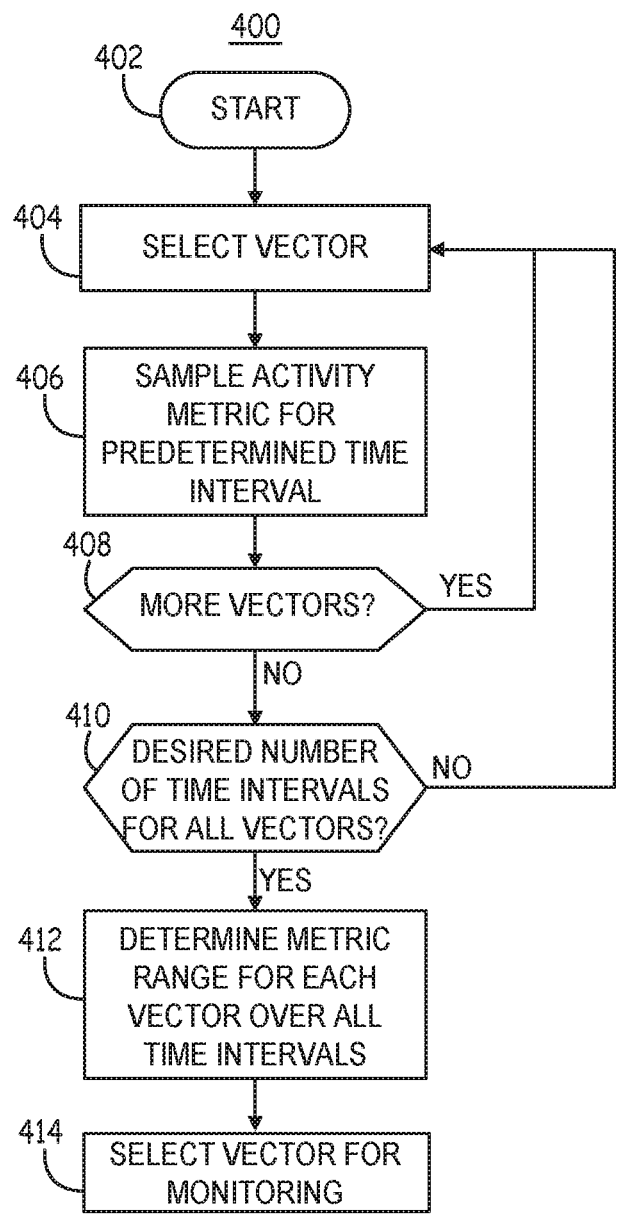
FIG. 6 is a flow chart of a method for selecting a vector for monitoring patient activity according to another embodiment.

FIG. 6 is a flow chart 400 of a method for selecting a vector for monitoring patient activity according to another embodiment. The process is started at block 402 in response to user input, a vector evaluation schedule, or another trigger as further described below. The process shown by FIG. 6 does not require detection of specific resting levels and non-resting levels of activity in order to begin acquiring data. Instead, a vector is selected at block 404, and the activity metric is sampled throughout a predetermined time interval at block 406 using the selected vector signal. For example, the activity metric may be determined every n seconds or minutes over a period of m hours. To illustrate, activity counts produced by a processor every 2 seconds may be averaged over one minute for a 24 hour period. During that 24-hour period, the patient is expected to engage in varying levels of activity. By sampling the activity count throughout a day, it is expected that counts are obtained during periods of rest and during periods of activity or exertion.

The activity metric is sampled at a predetermined sampling rate over a predetermined time interval for each vector being evaluated. Once data for the predetermined time interval has been obtained for all vectors, as determined at decision block 408, the process may be repeated for a desired number of time intervals for all vectors. For example, each vector may be selected for three 24-hour periods.

Once activity metrics have been sampled for all vectors for the desired number of time intervals, as determined at decision block 410, a metric range is determined for each vector at block 412. A vector resulting in the greatest range between a minimum activity metric (presumed to be rest) and a maximum activity metric (during exertion) is selected for monitoring patient activity at block 414.

To exclude outliers, averaging or selecting certain percentiles for determining the activity metric range may be used. For example, if 2-second activity counts are determined as the activity metric, the 2-second activity counts may be averaged over one minute or another predetermined interval. The highest and lowest one minute averages may be used to determine the vector range. In another example, a predetermined number of the lowest activity counts obtained over a 24-hour period may be averaged to determine the rest activity count. A predetermined number of the highest activity counts may be averaged to determine a maximum activity count. The averaged lowest counts and the averaged highest counts define the range of the activity metric for a given vector. Alternatively, percentiles could be used to select representative upper and lower boundaries of an activity metric range for a given vector. For example, all activity counts between the $95^{th}$ percentile and the $99^{th}$ percentile may be averaged to determine the maximum activity count value defining the upper range for a given vector.

The greatest range is expected to have the greatest signal to noise ratio when the sensor vector is subjected to other motion, such as cardiac motion when implanted in or near the heart. In this way, activity metrics for a first sensing condition, e.g. a low or resting level of activity and for a second sensing condition, e.g. a high or vigorous activity level, can be determined without detecting and reconfirming the sensing conditions prior to and after data acquisition as described in conjunction with FIG. 4.

Figure 7:
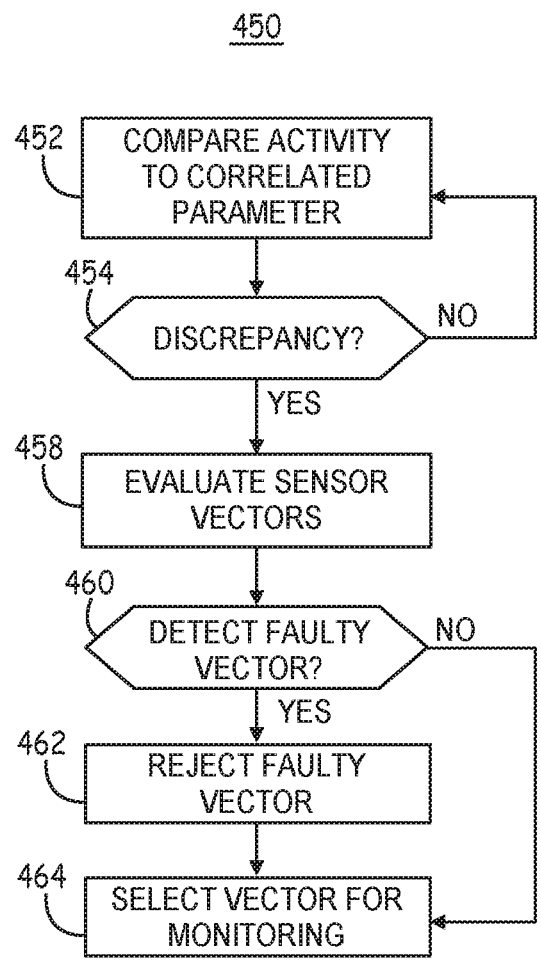
FIG. 7 is a flow chart of a method for triggering an evaluation of accelerometer vectors according to one example.

FIG. 7 is a flow chart 450 of a method for triggering an evaluation of accelerometer vectors according to one example. At block 452, the activity metric monitored for indicating patient activity is compared to a correlated physiological parameter derived from another sensor to determine if there is agreement between the currently detected patient activity level or trend in activity and the correlated parameter. For example, the activity metric may be compared to a heart rate determined from sensed electrical signals. If the heart rate is high but the activity metric is indicating a resting level, this discrepancy may indicate a bad accelerometer vector is being used for monitoring activity. If the heart rate is low, but the activity metric is indicating a high level of activity, the vector signal may have a low signal-to-noise ratio.

Accordingly, one trigger for evaluating the accelerometer vectors is a discrepancy between a current activity metric and a correlated physiological parameter, as detected at block 454. Comparisons may be made between the activity metric and a correlated physiological parameter on a periodic basis to monitor for a faulty sensor vector or loss of signal quality.

If a discrepancy is detected at block 454, the sensor vectors are evaluated at block 458 using the techniques described above in conjunction with FIG. 4 or 6 for acquiring activity metric data for available sensing vectors and selecting a sensing vector based on the data.

During the sensor vector evaluation, a faulty vector may be identified. For example, a vector may not be producing a signal that represents the full range of patient activity. A situation may exist in which the activity metric is not varying significantly from a resting value while heart rate is varying as expected between a resting heart rate and various active heart rates as the patient engages in various activities throughout the day. By periodically determining a relationship between activity and heart rate, a discrepancy in the activity metric can be recognized.

A vector may be identified as a faulty vector at block 460 when it does not change with patient activity based on a secondary parameter such as heart rate or based on comparisons between vectors. The vector identified as faulty may be rejected at block 462 for use in future patient monitoring. One of the remaining available vectors is selected at block 464 using criteria established to identify the vector producing an activity metric having a greatest difference between a resting level and an active level or the greatest activity metric range over a defined period of time.

Figure 8:
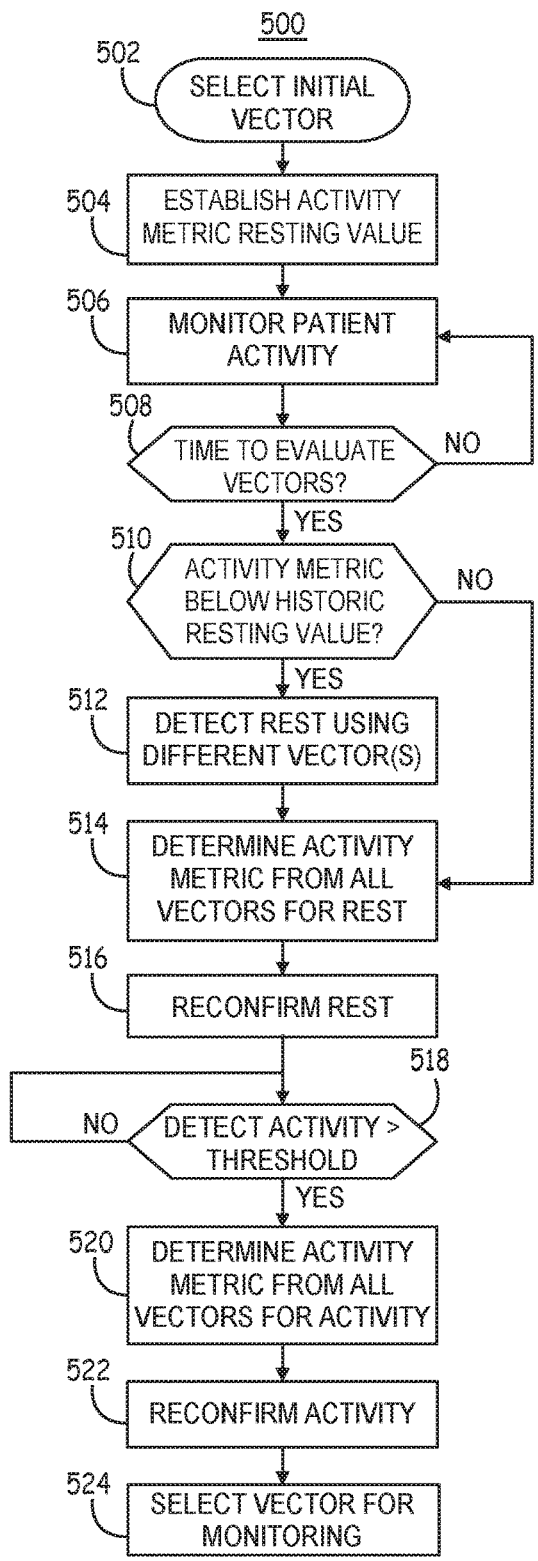
FIG. 8 is a flow chart of a method for selecting an activity sensor vector for monitoring patient activity according to another example.

FIG. 8 is a flow chart 500 of a method for selecting an activity sensor vector for monitoring patient activity according to another example. The method shown by flow chart 500 is useful for recognizing a faulty sensing vector that is being used for monitoring patient activity and selecting a different vector for patient monitoring. At block 502, an initial sensing vector is selected. The initial vector may be a nominal vector and may be verified by a clinician or technician as having an acceptable signal to noise ratio for monitoring patient activity.

A value of the activity metric that is derived from the selected accelerometer vector signal as being indicative of patient rest is established at block 504. In examples that position the accelerometer in or near the heart subjecting the accelerometer vectors to cardiac motion, cardiac motion will contribute significantly to the accelerometer signal at rest. The cardiac motion artifact is expected to be considerably higher when the accelerometer is positioned within the heart than when the accelerometer is positioned outside the heart, such as in a pectoral, abdominal or peripheral site. An activity count or other metric that includes cardiac motion artifact at rest is established to set a resting value or threshold of the activity metric.

Monitoring of patient activity is performed at block 506 using one or more activity metrics derived from the selected vector signal. The activity metric resting value may continue to be updated during patient monitoring to establish and maintain a historic resting value. Monitoring continues using the selected vector until the IMD processor determines it is time to evaluate the accelerometer vectors (block 508). This determination at block 508 may be based on a scheduled time, a user command, or one or more triggers as disclosed herein.

At block 510, the activity metric is compared to the historically established resting value. If the currently selected vector has not produced activity metric values less than the historically established resting value, the vector is considered valid and working. The valid vector is used to detect a resting condition for starting vector evaluation as described in conjunction with FIG. 4. Activity metric data is acquired for all available vectors at block 514.

If the activity metric for the currently selected vector is significantly below the established historic resting value, the vector may be broken or stuck. If the currently selected vector is producing a low level metric that is less than the established resting level, the selected vector is not reliable for verifying a resting condition and an activity condition during the sensor vector evaluation process. Instead, a resting condition is detected using one or more of the other available vectors at block 512. The activity metric is determined for all vectors during the detected resting condition at block 514 as described previously, e.g. for one or more consecutive or non-consecutive time intervals.

A low level activity metric may also be used as the trigger that initiates sensor vector evaluation at block 508. An activity metric that remains below the historically established activity metric resting value for a predetermined interval of time or predetermined number of time intervals may indicate a broken or stuck accelerometer vector.

At block 516, the resting condition of the patient may be reconfirmed using whichever vector or combination of vectors that was used to detect rest before acquiring activity metric data for the resting condition. Once activity metrics for a validated resting condition of the patient are acquired for all vectors, the process advances to block 518 to acquire data during patient activity.

At block 518, an activity level greater than a predetermined threshold is detected using one or more vectors. Similar to verifying the resting condition, an active condition is verified using the currently selected vector as long as it has not been disqualified due to too low of a signal level. Otherwise, one or more of the remaining available vectors are used to detect activity greater than a predetermined threshold at block 518.

Once a non-resting activity level is detected, the activity metric is determined for all available vectors at block 520. The activity level may be reconfirmed at block 522 to promote valid acquisition of activity metrics from all vectors during the same or similar level of activity. Using the activity metrics determined for each vector during rest and activity, a vector is selected at block 524 for monitoring patient activity, for example based on a greatest difference between the resting value and the active value of the metric for a given vector.

Figure 9A:
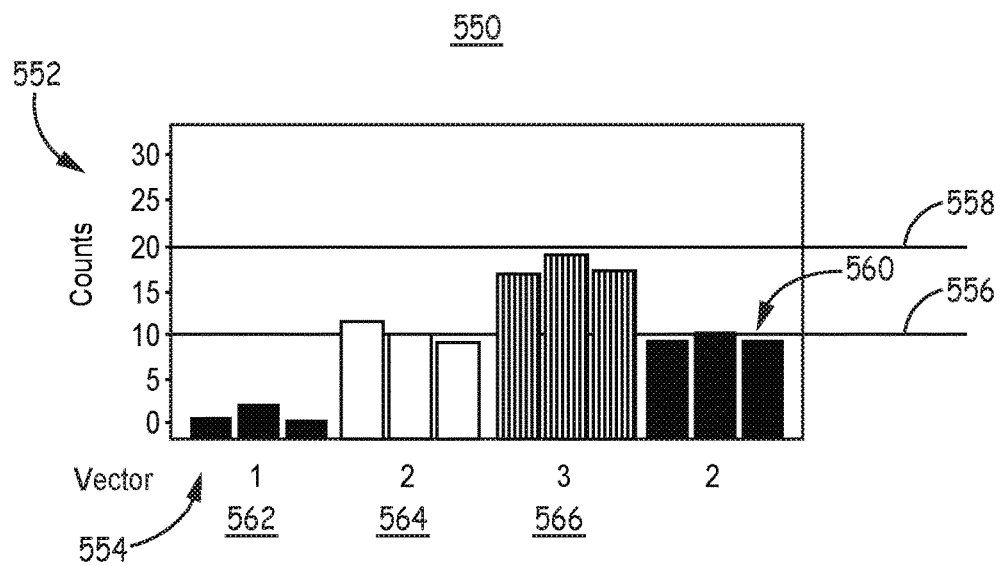
FIGS. 9A and 9B are example bar graphs of activity counts taken during rest and activity using three different accelerometer vectors.

FIG. 9A is an example bar graph of activity counts, shown along Y-axis 552, taken during rest using three different accelerometer vectors (562, 564, and 566 shown along X-axis 554). In this example, Vector 1 (562) is the programmed vector for monitoring patient motion. A historically established resting level 556 represents the activity count at rest that includes artifact due to cardiac motion present in the accelerometer signal when the patient is at rest. In addition to the resting level 556, an activities of daily living (ADL) level 558 has been established which indicates a level up to which activity accounts indicate normal daily activities of the patient, such as walking, moving around the home, and other non-strenuous or non-vigorous activity. Activity counts greater than the ADL level 558 indicate increased activity associated with exercise or exertion.

At the time of accelerometer evaluation, Vector 1 562 results in an activity count that is significantly less than the established historic resting activity count level 556. In one example, if the activity count is less than the historical resting level 556 for several minutes, a faulty accelerometer is suspected. As a result of the low level signal on Vector 1, Vector 2 (564) or Vector 3 (566) or a combination of both is selected for detecting rest. The activity counts obtained from Vector 2 are consistent with the historical resting level 556. Vector 2 is used for detecting rest, and activity counts are determined for both Vector 2 (564) and Vector 3 (566) for a desired number of time intervals. The resting condition is reconfirmed using Vector 2 at 560.

Figure 9B:
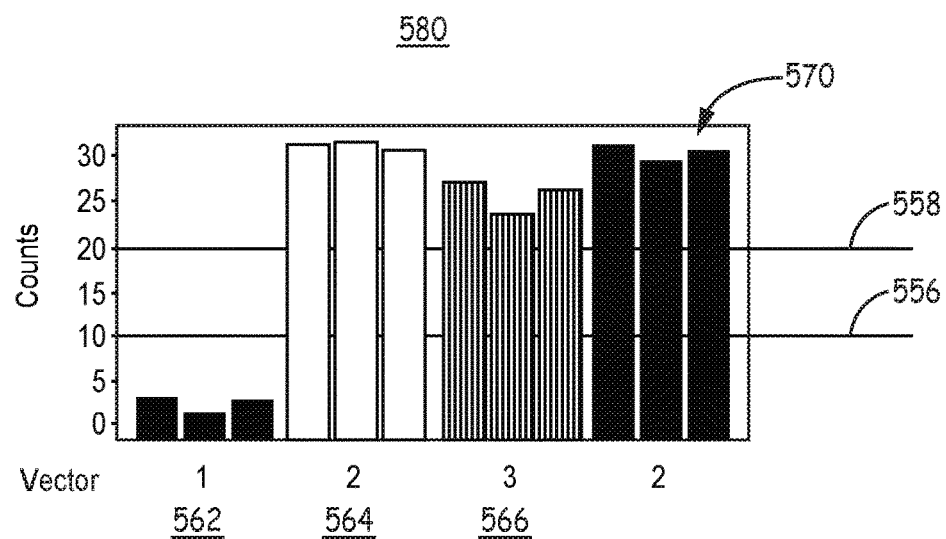

FIG. 9B is an example bar graph 580 of activity counts determined during patient activity after acquiring the resting data shown in FIG. 9A. After verifying the resting condition using Vector 2, Vector 2 is also used to monitor activity until an activity count greater than the ADL level 558 is detected. Activity counts for each of the vectors are determined for a desired number of time intervals. The activity counts from Vector 2 may be rechecked at 570 to verify the patient's active condition has not fallen below the ADL level 558 during the data acquisition.

The difference between the activity counts from Vector 1 at rest and activity clearly indicate a faulty vector. Vector 1 activity counts during activity remained below the established resting level 556. Vector 1 is therefore rejected for use in patient monitoring. Vector 2 presented the greatest difference in activity counts between rest and activity and is selected for monitoring patient activity.

Figure 10:
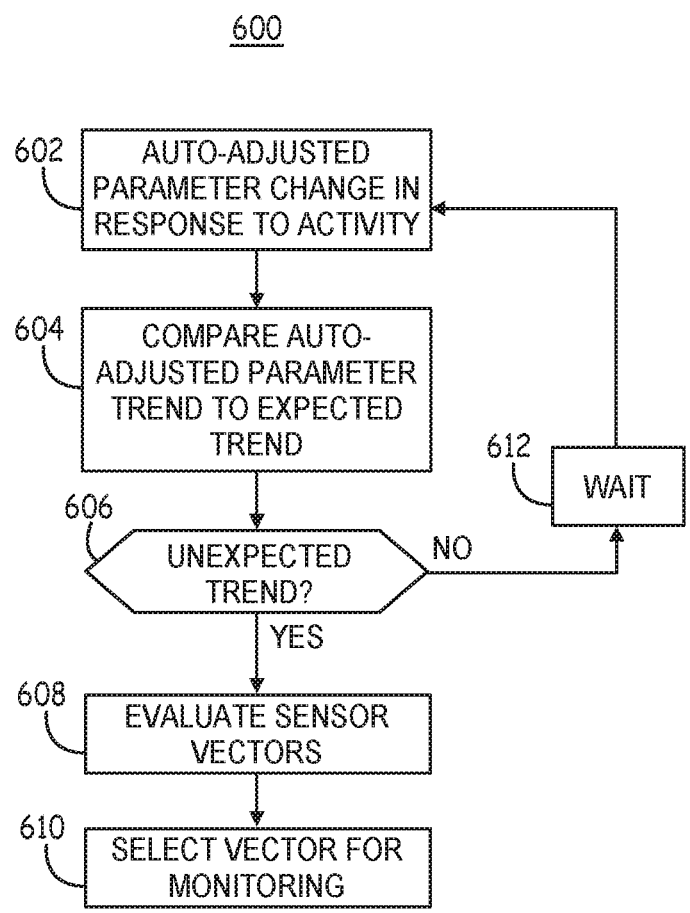
FIG. 10 is a flow chart of a method for controlling accelerometer vector selection according to one embodiment.

FIG. 10 is a flow chart 600 of a method for controlling accelerometer vector selection according to one embodiment. In some examples, the activity metric determined from an accelerometer vector signal is used in automatically adjusting a therapy delivery parameter. One method for determining when the accelerometer vector is no longer providing a reliable signal is to monitor the value, trend, and/or frequency that an auto-adjusted control parameter is adjusted based on the activity metric. For example, if the parameter is being changed too often, hasn't changed at all in a longer time than expected, has been sequentially increased multiple times or sequentially decreased multiple times, has reached a minimum or maximum value, or presented other behavior that deviates from an expected or desired trend, the accelerometer vector may be unreliable.

Accordingly, when a therapy control parameter is automatically adjusted in response to an activity metric at block 602, the value or trend of the auto-adjusted parameter is compared to an expected range or trend at block 604. If the therapy control parameter is within expected bounds or trends, as determined at block 606, the processor waits at block 612 until the next adjustment is made to the therapy control parameter at block 602. If the auto-adjusted parameter fails to meet an expected trend (or presents an unexpected trend), the accelerometer vectors are evaluated at block 608. Based on the evaluation, a new vector may be selected for monitoring patient activity at block 610 according to the techniques described above.

Figure 11:
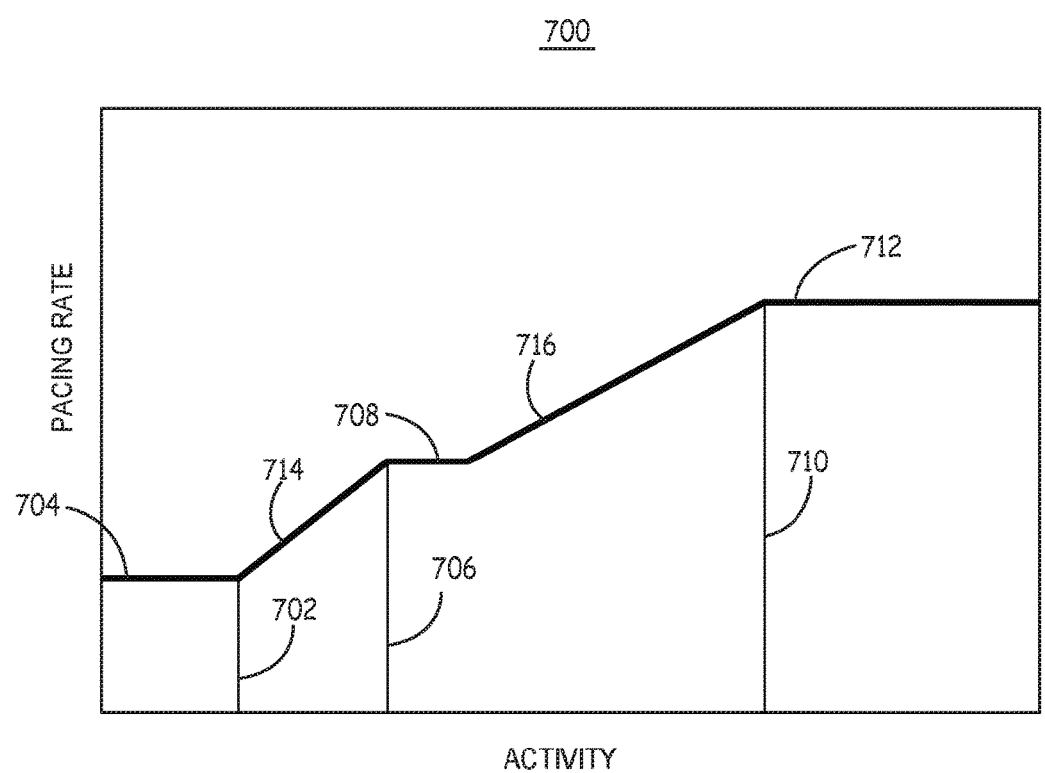
FIG. 11 is a plot illustrating rate responsive pacing therapy control parameters that may be automatically adjusted based on monitored patient activity.

FIG. 11 is a plot 700 illustrating rate responsive pacing therapy control parameters that may be automatically adjusted based on monitored patient activity. As patient activity level changes, pacing rate is adjusted according to a sensor-indicated pacing rate (SIR) computed from the activity metric and targeted pacing rates based on activity level setpoints. Activity metric thresholds or setpoints used for controlling the SIR may also be adjusted based on the patient's activity. For example, a lower pacing rate 704 may be set for activity metrics up to a baseline resting level of activity 702 that is expected to include cardiac motion noise when the IMD is implanted within a heart chamber. An ADL pacing rate 708 is defined for an ADL level 706 (or range) of the activity metric. The pacing rate is adjusted according to a slope or transfer function 714 defined by the LR 704 and the ADL rate 708 as the activity metric changes between the baseline resting level 702 and the ADL rate 708. The ADL rate 708 may be a targeted pacing rate determined to be optimal for the particular patient's normal daily activities.

An upper rate (UR) limit 712 defines a maximum pacing rate for a maximum expected activity level 710. The SIR used to pace the patient's heart is adjusted according to a slope or transfer function 716 as the patient's activity varies between the ADL level 706 and the maximum activity level 710.

The baseline resting level 702 that controls when the lower pacing rate 704 is delivered, the ADL level 706 that controls when a change between the transfer functions 714 and 716 is made for determining a SIR, and the maximum activity level 710 used to control when the maximum upper rate 712 is delivered may all be adjusted based on monitored activity. For example, the ADL level 706 (at which ADL rate 708 is applied) may be adjusted based on a patient's monitored activity over time. Trends and averages of the activity count determined over 24 hour periods may be used to generate a patient activity profile for setting the ADL level 706 and the maximum activity level 710, for example.

A rate profile optimization may be performed based upon daily or other longer-term activity data. The IMD processor may generate setpoints in order to influence the pacing rate to achieve optimal rates for patient need. The ADL setpoint 706 is set for determining when the target ADL pacing rate 708 is applied based on the patient profile. The ADL pacing rate 708 is generated based upon a pacing rate believed to be optimum for the daily activities for a patient. A device and methods for establishing activity metric setpoints for controlling pacing rate are disclosed in the above-incorporated '772 patent (Condie, et al.).

Figure 12:
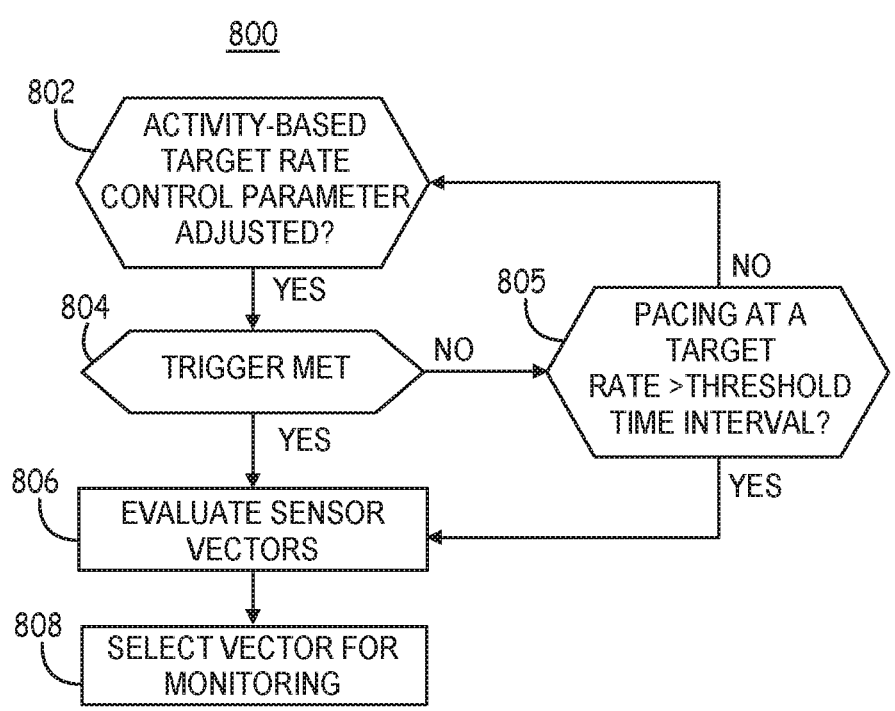
FIG. 12 is a flow chart of a method for controlling accelerometer vector selection based on the behavior of an auto-adjusted rate-responsive pacing control parameter.

FIG. 12 is a flow chart 800 of a method for controlling accelerometer vector selection based on the behavior of an auto-adjusted rate-responsive pacing control parameter. In delivering rate responsive cardiac pacing, the pacing rate is adjusted according to a SIR within the operating parameters defined by the target rates and associated setpoints as shown in FIG. 11. Accordingly, a trigger for evaluating accelerometer vectors may be based on adjustments to the SIR not meeting expected criteria. In other words, the delivered pacing rate may be monitored to determine if an unexpected trend in pacing rate is detected. If so, the accelerometer vector may be sub-optimal or faulty. Additionally or alternatively, a trigger for vector evaluation is based on adjustments to the setpoints used to set the target pacing rates (i.e. a LR, ADL rate and/or UR). The setpoints are based on historic patient activity profiles and an unexpected value or trend of the setpoints may indicate an unacceptable accelerometer vector.

FIG. 12 represents a method that combines both of these types of triggers for evaluating accelerometer vectors, i.e. a trigger based on the trend of the SIR pacing rate and a trigger based on the trend of the automatically adjusted setpoints used to control target pacing rates. In other implementations one or the other of these types of triggers may be used.

At block 802, if an activity-based target rate control parameter is adjusted based on patient activity monitored using an accelerometer vector, the IMD processor determines if a trigger for evaluating accelerometer vectors is met at block 804. The trigger represents criteria relating to the value or trend of the adjusted target rate control parameter.

In one example with reference to FIG. 11, rate responsive pacing setpoints (e.g. 702, 706, and 710) for controlling the LR, ADL rate, and UR (704, 708, and 712, respectively) may be set every twenty-four hours based on the patient's activity monitored during the previous day. If the LR setpoint 702 is decreased a certain number of days in a row, e.g. four consecutive days, an accelerometer vector evaluation is triggered. Low level activity metrics due to a faulty vector may be causing the LR setpoint 702 to be repeatedly reduced. In another example, if a lower rate setpoint and an ADL setpoint are less than a threshold difference apart, i.e. slope 714 becomes too steep, a vector evaluation is triggered at block 804.

In various embodiments, one or more trigger criteria may be defined relating to LR setpoint 702, ADL setpoint 706 and UR setpoint 710 or combinations thereof that trigger a vector evaluation. The criteria may include consecutive decreases, consecutive increases, reaching a maximum or minimum allowable value, setpoints being too close together or too far apart or resulting in too high or too low of slopes 714 and 716 between set points. Depending on the particular algorithm or control parameters being used to control target pacing rates during rate responsive pacing, numerous criteria can be conceived for causing an evaluation of the accelerometer vectors based on a value or trend of one or more target rate control parameters that are automatically adjusted based on monitored activity.

If trigger criteria are met (block 804), the accelerometer vectors are evaluated at block 806 according to the methods described above. A new vector may be selected for monitoring patient activity at block 808 if the currently selected vector no longer meets acceptable signal-to-noise ratio or another vector results in a better signal-to-noise ratio. It is recognized that various criteria may be applied to the vector activity metric data at block 808 for selecting an optimal or acceptable vector for a particular patient monitoring application. Examples of selection criteria include the maximum rest-to-activity ratio or maximum range of activity metrics over a predetermined time interval as described above, but other criteria could be conceived and defined.

If trigger criteria based on adjustments to target rate control parameters, such as setpoints, are not met at block 804, the trend of the SIR pacing rate may be examined at block 805. One or more triggers relating to the delivered pacing rate may be defined which cause accelerometer vector evaluation. For example, if the delivered pacing rate remains at a target rate (the LR, ADL rate or UR) for a threshold interval of time, a vector evaluation is performed at block 806. Separate threshold time intervals may be defined for each target rate. For example, if pacing is delivered at the LR for more than 3 days without increasing and the patient has historically been paced at the ADL rate and above the ADL rate on a daily basis, vector evaluation is triggered. If the patient is paced at the UR for more than one hour and has historically not remained at an activity level producing the UR as the SIR for more than a 20 minute interval, the vector evaluation is triggered at block 806.

The trigger criteria relating to delivered pacing rate behavior is not limited to the time intervals spent pacing at the LR, ADL rate and UR only. For example, if the pacing rate remains along slope 714 or slope 716 for more than a threshold interval of time, the vector evaluation may be triggered. These and other criteria may be used for triggering a vector evaluation based on a delivered sensor-indicated pacing rate trend. A new vector may be selected at block 808 based on the evaluation data.

If pacing at a target rate has not occurred for greater than a threshold interval of time, as determined at block 805, the process returns to block 802. The processor continues to monitor for target rate adjustment triggers (block 804) and pacing rate triggers (block 805) during the ongoing activity monitoring and rate responsive pacing therapy.

It is recognized that the techniques disclosed in the flow charts presented herein may be combined in different combinations than those shown and described here. For example, various combinations of triggers for causing vector evaluations and various techniques for acquiring vector signal data may be used for evaluating and selecting an accelerometer vector for patient monitoring other than the specific examples described herein.

Thus, various embodiments of a medical device and method have been described for selecting a vector of a multi-dimensional sensor for monitoring a patient. However, one of ordinary skill in the art will appreciate that various modifications may be made to the described embodiments without departing from the scope of the following claims.

The invention claimed is:

1. A method performed by an implantable medical device, the method comprising:
   receiving, by a processor of an implantable medical device having a multi-dimensional accelerometer, a signal from each vector of a plurality of vectors of the multi-dimensional accelerometer;
   determining, by the processor, a first value of a patient activity metric indicative of body motion from the signal for each vector of the plurality of vectors during a first sensing condition;
   determining, by the processor, a second value of the patient activity metric from the signal for each vector of the plurality of vectors during a second sensing condition;
   for each vector of the plurality of vectors, determining, by the processor, a difference between the first value and the second value of the patient activity metric determined for the first sensing condition and the second sensing condition, respectively;
   selecting, based upon the determined differences, a vector for monitoring the patient from the plurality of vectors of the multi-dimensional accelerometer;
   in response to selecting the vector for monitoring the patient, determining a third value of the patient activity metric indicative of body motion, the third value based only on the signal from the selected vector; and controlling, by the processor, a therapy rate delivered to the patient by adjusting a therapy delivery control parameter based on the third value of the patient activity metric indicative of body motion that has been determined based only on the signal from the selected vector for monitoring the patient.

2. The method of claim 1, wherein the implantable multi-dimensional accelerometer comprises a three-dimensional accelerometer.

3. The method of claim 1, wherein:
the first sensing condition is a patient resting condition, and
the second sensing condition is a non-resting condition.

4. The method of claim 1, further comprising:
establishing a historical value of the patient activity metric for the first sensing condition;
triggering the evaluating of the plurality of vectors in response to patient monitoring resulting in the patient activity metric not meeting the historical value for a predetermined interval of time.

5. The method of claim 1, further comprising:
comparing the adjusted therapy control parameter to an expected trend of the therapy control parameter; and
automatically triggering the evaluating of the plurality of vectors in response to the comparing.

6. The method of claim 1, wherein the therapy control parameter is a parameter for controlling rate responsive cardiac pacing.

7. The method of claim 6, wherein the therapy control parameter is an activity level setpoint that is used to set a target pacing rate.

8. The method of claim 1, further comprising determining a plurality of values of the patient activity metric for each of the plurality of vectors over a predetermined number of time intervals.

9. The method of claim 8, wherein determining the first value of the patient activity metric for the first sensing condition and determining the second value of the patient activity metric for the second sensing condition comprises determining a range of the plurality of values of the patient activity metric over the predetermined number of time intervals for each of the plurality of vectors.

10. The method of claim 1, further comprising:
determining a plurality of values of the patient activity metric at predetermined intervals of time using the selected vector;
controlling a therapy control parameter in response to the plurality of values of the patient activity metric;
generating a historical profile of the patient activity metric;
automatically adjusting an activity setpoint for controlling a targeted rate of therapy delivery in response to the historical profile;
comparing the automatically adjusted setpoint to a trend criteria; and
triggering the evaluating in response to the automatically adjusted activity setpoint not meeting the trend criteria.

11. The method of claim 1, further comprising:
confirming the first sensing condition after determining the first value of the patient activity metric for each of the plurality of vectors during the first sensing condition; and
confirming the second sensing condition after determining the second value of the patient activity metric for each of the plurality of vectors during the second sensing condition.

12. An implantable medical device, comprising:
a multi-dimensional accelerometer comprising a plurality of vectors for sensing motion; and
a processor configured to:
evaluate the plurality of vectors by:
receiving a signal from each vector of the plurality of vectors of the multi-dimensional accelerometer;
determining a first value of a patient activity metric indicative of body motion from the signal for each vector of the plurality of vectors during a first sensing condition;
determining a second value of the patient activity metric from the signal for each vector of the plurality of vectors during a second sensing condition;
for each vector of the plurality of vectors, determining a difference between the first value and the second value of the patient activity metric determined for the first sensing condition and the second sensing condition, respectively; and
selecting, based upon the determined differences, a vector for monitoring the patient from the plurality of vectors of the multi-dimensional accelerometer;
in response to selecting the vector for monitoring the patient, determine a third value of the patient activity metric indicative of body motion, the third value based only on the signal from the selected vector; and
control a therapy rate delivered to the patient by adjusting a therapy delivery control parameter based on the third value of the patient activity metric indicative of body motion that has been determined based only on the signal from the selected vector for monitoring the patient.

13. The device of claim 12, wherein the accelerometer is a three-dimensional accelerometer having three orthogonal vectors.

14. The device of claim 12, wherein the processor is configured to:
determine the first value of the patient activity metric for the first sensing condition when the patient is at rest, and
determine the second value of the patient activity metric for the second sensing condition when the patient is not at rest.

15. The device of claim 12, wherein the processor is further configured to:
establish a historical value of the patient activity metric for the first sensing condition; and
trigger the evaluating of the plurality of vectors in response to patient monitoring resulting in the patient activity metric not meeting the historical value for a predetermined interval of time.

16. The device of claim 12,
wherein the processor is further configured to:
compare the adjusted therapy control parameter to an expected trend of the therapy control parameter; and
automatically trigger the evaluating of the plurality of vectors in response to the comparing.

17. The device of claim 16, wherein the therapy control parameter is a parameter for controlling rate responsive cardiac pacing.

18. The device of claim 17, wherein the therapy control parameter is an activity level setpoint that is used to set a target pacing rate.

19. The device of claim 12, wherein the processor is further configured to:
determine a plurality of values of the patient activity metric for each of the plurality of vectors over a predetermined number of time intervals.

20. The device of claim 19, wherein determining the first value of the patient activity metric for the first sensing condition and determining the second value of the patient activity metric for the second sensing condition comprises determining a range of the plurality of values of the patient activity metric over the predetermined number of time intervals for each of the plurality of vectors.

21. The device of claim 12, wherein the processor is further configured to:
   determine a plurality of values of the patient activity metric at predetermined intervals of time using the selected vector;
   control a therapy control parameter in response to the plurality of values of the patient activity metric;
   generate a historical profile of the patient activity metric;
   automatically adjust an activity setpoint for controlling a targeted rate of therapy delivery in response to the historical profile;
   compare the automatically adjusted activity setpoint to a trend criteria; and
   trigger the evaluating in response to the automatically adjusted activity setpoint not meeting the trend criteria.

22. The device of claim 12, wherein the processor is further configured to:
   confirm the first sensing condition after determining the first value of the patient activity metric for each of the plurality of vectors during the first sensing condition; and
   confirm the second sensing condition after determining the second value of the patient activity metric for each of the plurality of vectors during the second sensing condition.

23. A non-transitory computer readable storage medium storing a set of instructions that cause a processor of an implantable medical device comprising a multi-dimensional accelerometer to:
   receive a signal from each vector of a plurality of vectors of the multi-dimensional accelerometer;
   determine a first value of a patient activity metric indicative of body motion from the signal for each vector of the plurality of vectors during a first sensing condition;
   determine a second value of the patient activity metric from the signal for each vector of the plurality of vectors during a second sensing condition;
   for each vector of the plurality of vectors, determine a difference between the first value and the second value of the patient activity metric determined for the first sensing condition and the second sensing condition, respectively;
   select, based upon the determined differences, a vector for monitoring the patient from the plurality of vectors of the multi-dimensional accelerometer;
   in response to selecting the vector for monitoring the patient, determine a third value of the patient activity metric indicative of body motion, the third value based only on the signal from the selected vector; and
   control a therapy rate delivered to the patient by adjusting a therapy delivery control parameter based on the third value of the patient activity metric indicative of body motion that has been determined based only on the signal from the selected vector for monitoring the patient.

24. The method of claim 1, wherein:
   determining the first value of the patient activity metric during the first sensing condition comprises determining the patient activity metric during a resting condition of the patient;
   determining the second value of the patient activity metric during the second sensing condition comprises determining the patient activity metric during a non-resting condition of the patient; and
   selecting the vector of the multi-dimensional accelerometer comprises selecting the vector having a greatest difference between the first value of the patient activity metric and the second value of the patient activity metric for respective vectors of the plurality of vectors;
   the method further comprising monitoring the patient by determining a sensor indicated pacing rate from the signal of the selected vector of the plurality of vectors; and
   controlling a pulse generator, by the processor, to deliver cardiac pacing pulses at the determined sensor indicated pacing rate.

* * * * *